(12) United States Patent
Treado et al.

(10) Patent No.: US 7,692,776 B2
(45) Date of Patent: Apr. 6, 2010

(54) CHEMICAL IMAGING EXPLOSIVES (CHIMED) OPTICAL SENSOR

(75) Inventors: Patrick J. Treado, Pittsburgh, PA (US); Matthew P. Nelson, Harrison City, PA (US)

(73) Assignee: Chem Image Corporation, Pittsburgh, PA (US)

( * ) Notice: Subject to any disclaimer, the term of this patent is extended or adjusted under 35 U.S.C. 154(b) by 461 days.

(21) Appl. No.: 11/645,132

(22) Filed: Dec. 22, 2006

(65) Prior Publication Data
US 2009/0303471 A1 Dec. 10, 2009

Related U.S. Application Data

(60) Provisional application No. 60/754,011, filed on Dec. 23, 2005.

(51) Int. Cl.
G01N 21/00 (2006.01)

(52) U.S. Cl. .................. 356/73; 356/317; 356/301

(58) Field of Classification Search ............. 356/72–73, 356/301, 317–318, 417
See application file for complete search history.

(56) References Cited

U.S. PATENT DOCUMENTS

| 6,421,553 | B1 | 7/2002 | Costa et al. |
| 2003/0085348 | A1* | 5/2003 | Megerle ............ 250/287 |
| 2004/0051867 | A1 | 3/2004 | Brestel et al. |
| 2006/0077377 | A1* | 4/2006 | Brestel et al. ............. 356/72 |
| 2006/0219937 | A1* | 10/2006 | Henry et al. ............. 250/425 |
| 2008/0165344 | A1* | 7/2008 | Treado et al. ............. 356/72 |
| 2008/0192246 | A1* | 8/2008 | Neiss et al. ............. 356/301 |

FOREIGN PATENT DOCUMENTS

WO PCT/US06/49176 7/2008

OTHER PUBLICATIONS

Sharma, S.K., et al., "Combined remote LIBS and Raman spectroscopy of minerals using a single laser source," (2007), Lunar Planet. Sci. XXXVIII.
Clegg, S.M., et al., "LIBS-Raman spectroscopy of minerals using remote surface modification techniques," (Mar. 2006), Lunar Planet. Sci. XXXVII.

(Continued)

*Primary Examiner*—Kara E Geisel
(74) *Attorney, Agent, or Firm*—Morgan Lewis & Bockius

(57) ABSTRACT

A system and method of detecting explosive compounds located on a sample. The sample is irradiated with animal-safe ultra-violet radiation generating a fluorescence data set. A fluorescence database is searched based on the fluorescence data set in order to identify a known fluorescence data set. If the searching of the fluorescence database identifies a known fluorescence data set, an area of interest in the sample is identified based on the known fluorescence data set identified in the fluorescence database searching. The area of interest is irradiated with substantially monochromatic radiation to generate a Raman data set of the area of interest. A Raman database is searched based on the Raman data set in order to identify a known Raman data set. An explosive compound in the area of interest is identified based on the known Raman data set identified by searching the Raman database.

15 Claims, 8 Drawing Sheets

OTHER PUBLICATIONS

Thompson, J., et al., Combined remote LIBS and Raman spectroscopy measurements. Lunar Planet. Sci., XXXVI, 2005.

Wiens, R.C., Development of a prototype laser-induced breakdown spectroscopy (LIBS) instrument with stand-off Raman capabilities as part of the Mars Instrument Development Program, Lunar Planet. Sci., XXXI.

"Poster Session: Mars Polar Science, Astrobiology, Future Missions/Instruments and Other Mars Science," (Jul. 2007), Seventh International Conference on Mars, Session 11.

Marquardt, Brian J., et al., "Novel Probe for Laser-Induced Breakdown Spectroscopy and Raman Measurements Using an Imaging Optical Fiber," (Jun. 1998) vol. 52, No. 9.

* cited by examiner

CHEMICAL IMAGING EXPLOSIVES (CHIMED) OPTICAL SENSOR

RELATED APPLICATIONS

This application claims the benefit of U.S. Provisional Application No. 60/754,011 entitled "Chemical Imaging Explosives (CHIMED) Optical Sensor," filed Dec. 23, 2005, which is incorporated herein by reference in its entirety.

FIELD OF DISCLOSURE

The present disclosure relates generally to a method and system to use spectroscopic measurements to identify an explosive compound using fluorescence and Raman imaging.

SUMMARY

The present disclosure provides for a method of detecting explosive compounds located on a sample. The sample includes items such as a human hand, a passport, a credit card, a driver's license, a boarding pass, a human body part, a human clothing, a human-wearable item, and an airline ticket. The sample is irradiated with animal-safe ultra-violet radiation to thereby generate emitted photons. A fluorescence data set is obtained based on the emitted photons. A fluorescence database is searched in accordance with the fluorescence data set in order to identify a known fluorescence data set from the fluorescence database. The fluorescence database contains a plurality of known fluorescence data sets. Each known fluorescence data set is associated with a known explosive compound. The known explosive compound includes compounds such as nitrocellulose, nitroglycerin, 1,3,5-trinitroperhydro-1,3,5-triazine ("RDX"), 1,3,5,7-tetranitroperhydro-1,3,5,7-tetrazocine ("HMX"), and 1,3-Dinitrato-2,2-bis (nitratomethyl)propane ("PETN"). If the searching of the fluorescence database identifies a known fluorescence data set, an area of interest in the sample is identified based on the known fluorescence data set identified in the fluorescence database searching. The area of interest is irradiated with substantially monochromatic radiation to generate scattered photons from the area of interest. A Raman data set is obtained based on the scattered photons. A Raman database is searched in accordance with the Raman data set in order to identify a known Raman data set from the Raman database. The Raman database contains a plurality of known Raman data sets. Each known Raman data set is associated with a known explosive compound. An explosive compound in the area of interest is identified based on the known Raman data set identified by searching the Raman database.

In one embodiment, the plurality of known fluorescence data sets includes one or more of the following: a plurality of fluorescence spectra corresponding to the known explosive compounds, and a plurality of spatially accurate wavelength resolved fluorescence spectroscopic images corresponding to the known explosive compounds.

In yet another embodiment, the plurality of known Raman data sets includes one or more of the following: a plurality of Raman spectra corresponding to the known explosive compounds and a plurality of spatially accurate wavelength resolved Raman spectroscopic images corresponding to the known explosive compounds.

In accordance with a further aspect, the disclosure provides for a method of detecting suspicious chemical substances located on a sample. A fluorescence emission signature of a sample is obtained. Whether a suspicious chemical substance is present in the sample is determined and a location of the substance in the sample is determined based on the fluorescence signature of the sample. The determined location of the sample is irradiated with substantially monochromatic radiation to thereby generate scattered photons. A Raman signature of the suspicious chemical substance is obtained based on the scattered photons. The suspicious chemical substance is identified based on a comparison of the Raman signature with a Raman database containing a plurality of Raman signatures associated with a corresponding plurality of known explosive materials.

In another embodiment, whether the suspicious chemical substance is present in the sample is determined by a series of steps. A fluorescence database is assessed where the fluorescence database contains a plurality of fluorescence signatures associated with a corresponding plurality of known suspicious chemical substances. The fluorescence emission signature is compared against the plurality of fluorescence signatures in the fluorescence database so as to determine whether one of the plurality of known suspicious chemical substances is present in the sample.

The present disclosure further provides for a storage medium containing machine readable program code, which, when executed by a processor, causes the processor to perform a series of steps. The sample is irradiated with animal-safe ultra-violet radiation to generate emitted photons. A fluorescence data set is obtained based on the emitted photons. A fluorescence database is searched in accordance with the fluorescence data set in order to identify a known fluorescence data set from the fluorescence database. If the searching of the fluorescence database identifies a known fluorescence data set, an area of interest in the sample is identified based on the known fluorescence data set identified in the fluorescence database searching. The area of interest is irradiated with substantially monochromatic radiation to generate scattered photons from the area of interest. A Raman data set is obtained based on the scattered photons. A Raman database is searched in accordance with the Raman data set in order to identify a known Raman data set from the Raman database. Each known Raman data set is associated with a known explosive compound. An explosive compound in the area of interest is identified based on the known Raman data set identified by searching the Raman database.

The present disclosure further yet provides for a system for detecting explosive compounds located on a sample. The system includes an animal-safe ultra-violet irradiation source, a substantially monochromatic irradiation source, a spectroscopic device, machine readable program code containing executable program instructions and a processor operatively coupled to the animal-safe ultra-violet irradiation source, the substantially monochromatic irradiation source and the spectroscopic device. The processor is configured to execute the machine readable program code so as to perform a series of steps.

In one embodiment, the system further includes a fluorescence database containing a plurality of known fluorescence data sets. The known fluorescence data sets include one or more of a plurality of fluorescence spectra corresponding to the known explosive compounds, and a plurality of spatially accurate wavelength resolved fluorescence spectroscopic images corresponding to the known explosive compounds.

In another embodiment, the system further yet includes a Raman data base containing a plurality of known Raman data sets. The known Raman data sets include one or more of a plurality of Raman spectra corresponding to the known explosive compounds and a plurality of spatially accurate wavelength resolved Raman spectroscopic images corresponding to the known explosive compounds.

BRIEF DESCRIPTION OF THE DRAWINGS

The accompanying drawings, which are included to provide further understanding of the disclosure and are incorporated in and constitute a part of this specification, illustrate embodiments of the disclosure and, together with the description, serve to explain the principles of the disclosure.

In the drawings.

DETAILED DESCRIPTION OF THE DISCLOSURE

Reference will now be made in detail to the preferred embodiments of the present disclosure, examples of which are illustrated in the accompanying drawings. Wherever possible, the same reference numbers will be used throughout the drawings to refer to the same or like parts.

The present disclosure provides for a sensor system and method to detect suspicious chemical substances on a sample such as a personal document, a hand or an object that a person provides for inspection. The sensor system and method are particularly suited for inspection of samples at sites such as an airport, seaport, country boarder crossing, points of inspection within the mail system and government or private businesses. The substance may be transferred on the sample by a person touching the sample where the individual has handled a material before coming to the various inspection sites. The substance may include explosive material, biohazards or an illegal substance. The substance may be identified by scanning the individual's hands and/or the relevant samples. The scanning may be conducted while the individual is waiting at the inspection sites such as an airport counter to obtain a boarding pass or automatic boarding pass kiosk or security checkpoint equipment. The sensor, of the present disclosure, may be place adjacent to the existing inspection site. The sensor may also be operatively linked to the existing inspection equipment permitting a single inspection process. When a suspicious material is identified, the identification is reported to the appropriate authorities. The reporting mechanism includes an audible alarm, a visible alarm, or an instant message to appropriate authorities.

Figure 1:
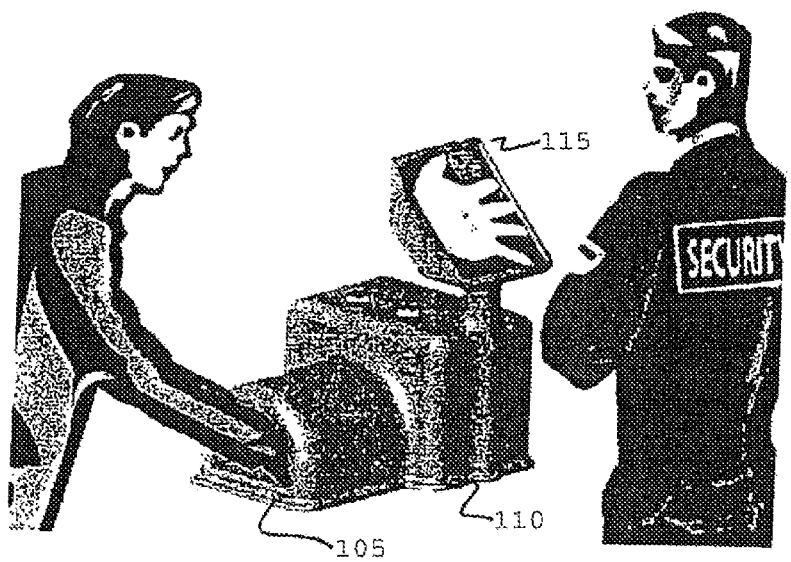
FIG. 1 schematically represents an exemplary senor system of the present disclosure.

FIG. 1 illustrates an exemplary sensor system 100 of the present disclosure. Sensor system 100 includes a sample chamber 105, a monitoring device 110 and a viewing screen 115.

Figure 2:
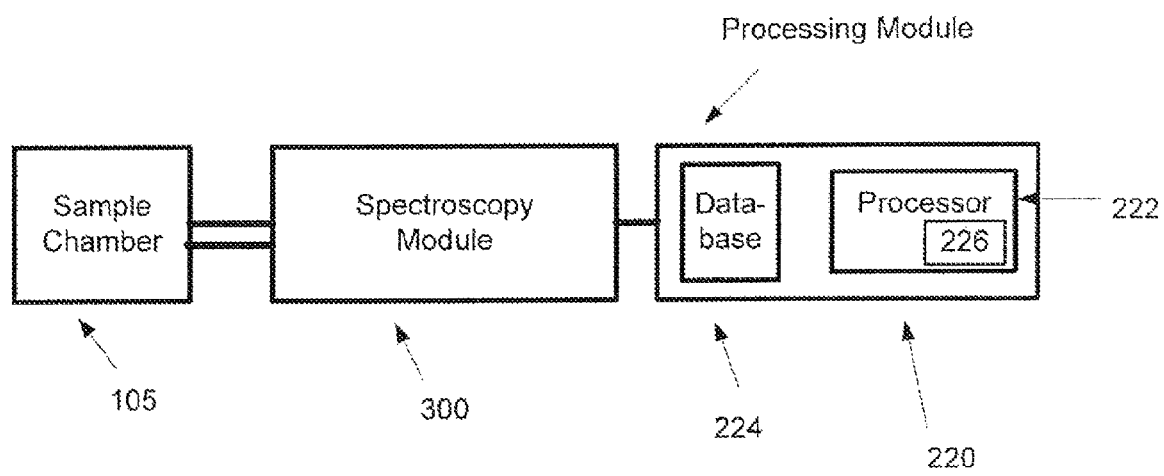
FIG. 2 schematically represents another exemplary senor system of the present disclosure.

FIG. 2 illustrates a second exemplary system 200 of the present disclosure. Sensor system 200 includes sample chamber 105, spectroscopy module 300 and processing module 220. Sample 201 is placed inside sample chamber 105 for analysis. Processing module 220 includes processor 222, database 224, and machine readable program code 226. The machine readable program code 228 contains executable program instructions. Processor 222 is configured to execute the machine readable program code 226 so as to perform the methods of the present disclosure.

Figures 3A, 3B:
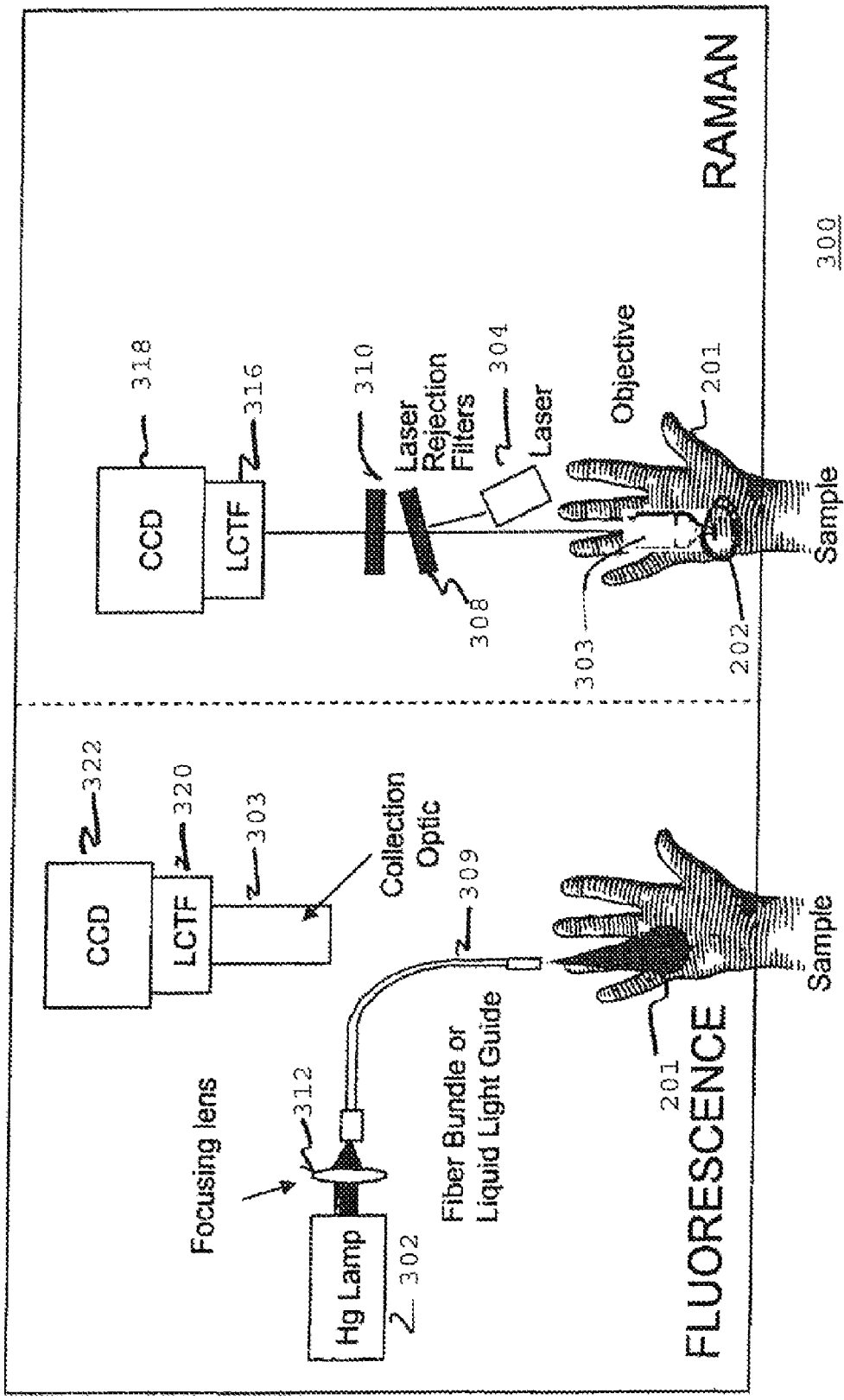
FIGS. 3A and 3B illustrate an exemplary spectroscopy module of the present disclosure.

FIGS. 3A and 3B illustrate an exemplary spectroscopy module 300 used to perform methods of the present disclosure. Spectroscopy module 300 includes components for fluorescence spectroscopy and Raman spectroscopy. To collect fluorescence data sets, spectroscopy module 300 employs collection optics 303, light source 302, focusing lens 312, light guide 309, a spectroscopic device in the form of fluorescence filter 320, and detector 322, FIG. 3A. To collect Raman data sets, spectroscopy module 300 employs objective 303, light source 304, a spectroscopic device in the form of imaging spectrometer 316, detector 318, and filters 308 and 310, FIG. 3B. Processor 226 is operatively coupled to light sources 302 and 304, the spectroscopic device in the form of fluorescence filter 320 and imaging spectrometer 316. Objective 303 is selected to obtain a desired working distance. In one embodiment, objective 303 has a numerical aperture of 0.46 and a working distance of 1 cm. In another embodiment, spectroscopy module 300 may be used to collect transmitted photons in the near infrared wavelength region.

Figures 4A, 4B:
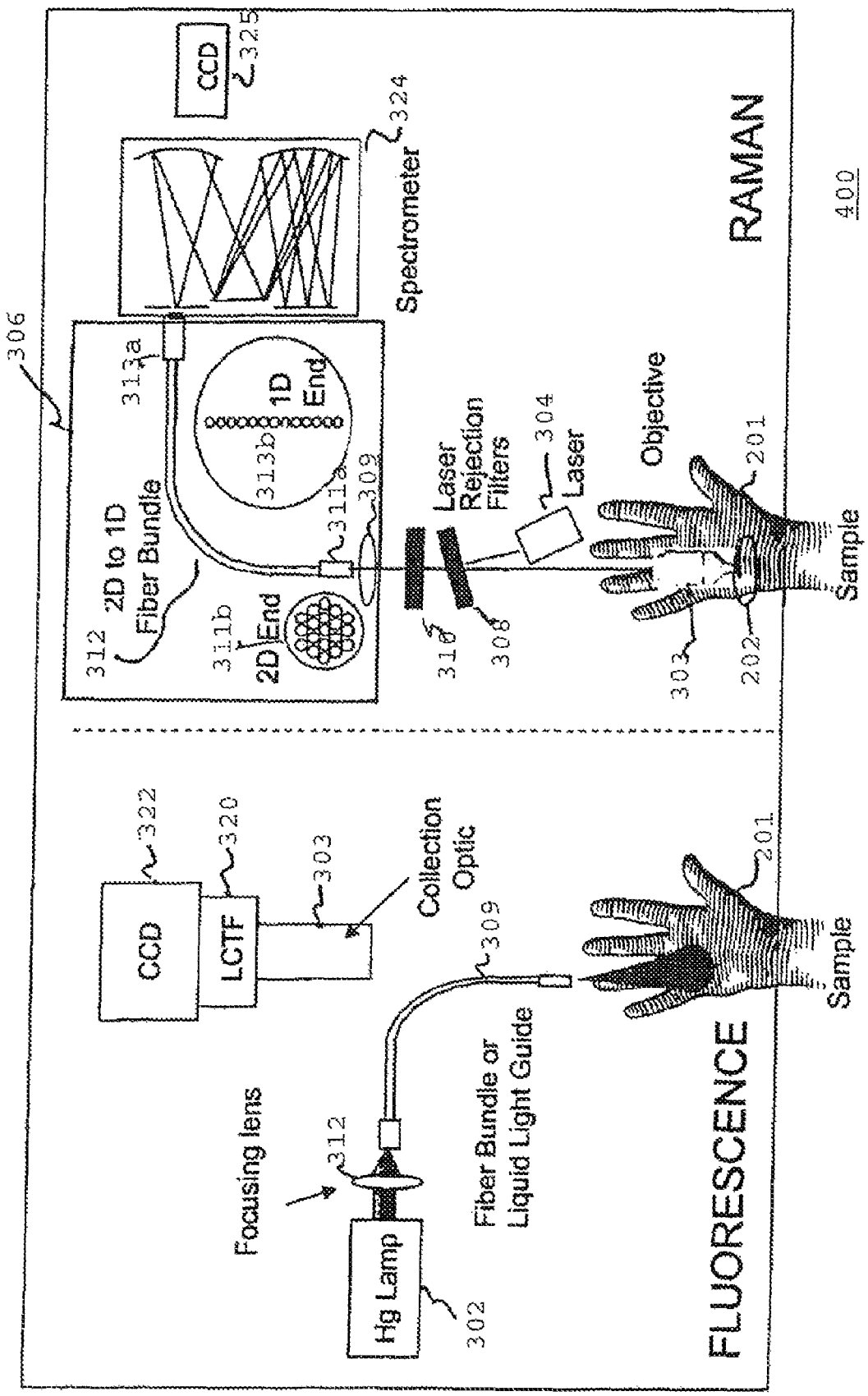
FIGS. 4A and 4B illustrate another exemplary spectroscopy module of the present disclosure.

FIGS. 4A and 4B illustrate another embodiment of an exemplary spectroscopy module 400 used to perform methods of the present disclosure. In this embodiment, the fluorescence data sets are collected with the components as described in FIG. 3A. To collect Raman data sets, spectroscopy module 400 employs objective 303, light source 304, filters 308 and 310, fiber array spectroscopic translator ("FAST") device 306, spectrometer 324 and detector 325, FIG. 4B. Processor 226 is operatively coupled to light sources 304, FAST device 306 and dispersive spectrometer 324. In another embodiment, spectroscopy module 400 may be used to collect transmitted photons in the near infrared wavelength region.

Sample 201 includes an animal's body party or any item handled by an animal having residue of suspicious chemical substance on the animal's body parts such as a hand. Representative examples of sample 201 include items such as a human hand, a passport, a credit card, a driver's license, a boarding pass, a human body part, a human clothing, a human-wearable item, and an airline ticket. As illustrated in FIGS. 3A and 3B, sample 201 may contain an area of interest 202 which generates a fluorescence data set indicative of a suspicious chemical substance, including an explosive compound or an additive and/or binder used to compound the explosive compound, biohazards or illegal substances.

Referring to FIGS. 3A and 4A, light source 302 is used to irradiate sample 201 with broad band light. In one embodiment, light source 302 includes animal-safe ultraviolet radiation. In one embodiment, light source 302 produces long wavelength or blacklight ultraviolet radiation ("UVA") having wavelengths ranging from 400 nm to 315 nm. In another embodiment, light source 302 produces long wavelength ultraviolet radiation UVB having wavelengths ranging from 315 nm to 280 nm. In yet another embodiment, light source 302 produces light at 365 nm.

Referring to FIGS. 3B and 4B, light source 304 is used to irradiate an area of interest 202 in sample 201 with substantially monochromatic light. Light source 304 can include any conventional photon source, including laser, LED, and other IR or near IR devices. The substantially monochromatic radiation reaching sample 201 illuminates the sample 201 to produce scattered photons from a suspicious chemical substance in the area of interest 202 of sample 201. Filters 308 and 310 reject light at the wavelength of laser light source 304.

With reference to FIGS. 3A and 4A, fluorescence filter 320 functions to produce fluorescence data sets of the sample. In one embodiment, the fluorescence data set includes a plurality of fluorescence spectra of a suspicious chemical substance on sample 201. In another embodiment, the fluorescence data set includes a plurality of spatially accurate wavelength resolved fluorescence images of suspicious chemical substance sample 201. A fluorescence spectrum of sample 210 contains a fluorescence emission signature of the suspicious chemical substance. This emission signature includes a wavelength band characteristic of a chemical functional group within the suspicious chemical substance. CCD detector 322 detects, in a spatially accurate manner, the emitted photons passed by fluorescence spectrometer 320.

Referring to FIG. 3B, imaging spectrometer 316 functions to produce Raman data sets of a suspicious chemical sample in area of interest 202. In one embodiment, the Raman data set includes a plurality of Raman spectra of the suspicious chemical substance. In another embodiment, the Raman data set includes a plurality of spatially accurate wavelength resolved Raman images of the suspicious chemical substance. A Raman spectrum contains a Raman signature of the suspicious chemical substance. This signature may include a wavelength band characteristic of a chemical functional group within the suspicious chemical substance. Detector 318 detects, in a spatially accurate manner, the Raman scattered photons passed by imaging spectrometer 316.

Referring again to FIGS. 3A and 3B, fluorescence filter 329 and imaging spectrometer 316 are used to generate the plurality of spatially accurate wavelength resolved spectroscopic fluorescence images and Raman images, respectively. Fluorescence filter 329 and imaging spectrometer 316 include a two-dimensional tunable filter, such as electro-optical tunable filters, liquid crystal tunable filter ("LCTF") or acousto-optical tunable filter ("AOTF"). The electro-optical filter (interchangeably, tunable filters) sequentially passes emitted photons or Raman scattered photons into a plurality of predetermined wavelength bands. The plurality of predetermined wavelength bands include specific wavelengths or ranges of wavelengths. In one embodiment, the predetermined wavelength bands include wavelengths characteristic of the sample undergoing analysis. The wavelengths that can be passed through fluorescence filter 329 and imaging spectrometer 316 may range from 200 nm (ultraviolet) to 2000 nm (i.e., the far infrared). The choice of tunable filter depends on the desired optical region and/or the nature of the sample being analyzed. The two-dimensional tunable filter includes a Fabry Perot angle tuned filter, an acousto-optic tunable filter, a liquid crystal tunable filter, a Lyot filter, an Evans split element liquid crystal tunable filter, a Solc liquid crystal tunable filter, a spectral diversity filter, a photonic crystal filter, a fixed wavelength Fabry Perot tunable filter, an air-tuned Fabry Perot tunable filter, a mechanically-tuned Fabry Perot tunable filter, a liquid crystal Fabry Perot tunable filter. The tunable filer is selected to operate in one or more of the following spectral ranges: the ultraviolet (UV), visible and near infrared.

Referring to FIG. 4B, the FAST device 306 receives the collected scattered photons produced by a suspicious chemical substance in area of interest 202. The FAST device 306 includes a first lens 309, a first end of a fiber bundle 311a and 311b, a fiber bundle 312, and a second end of the fiber bundle 313a and 313b which is connected to spectrometer 324. In the FAST device 306, a two-dimensional array of optical fibers is drawn into a one-dimensional fiber stack so as to effectively convert a two-dimensional field of view into a curvilinear field of view. The first end 311a of the fiber bundle 312 is comprised of a two dimensional non-linear array of fiber bundles 311b. The second end 313a of the fiber bundle 312 is comprised of a curvilinear array of fiber bundles 313b. The curvilinear array may include a straight line as well as curved line configurations. The entrance slit of spectrometer 324 is optically coupled to the FAST device 306 through the second end 313b of the fiber bundle 312. Spectrometer 324 disperses the scattered photons to generate a plurality of spatially resolved Raman spectra detected by detector 325.

Spectroscopy modules 300 and 400 include a plurality of detectors. Detectors 318, 322 and 325 may include a digital device such as for example an image focal plane array ("FPA") or CCD or CMOS sensor. The optical region employed to characterize the sample of interest governs the choice of two-dimensional array detector. For example, a two-dimensional array of silicon charge-coupled device ("CCD") detection elements can be employed with visible wavelength emitted photons or Raman scatter photons, while gallium arsenide (GaAs) and gallium indium arsenide (GaInAs) FPA detectors can be employed for image analyses at near infrared wavelengths. The choice of such devices depends on the type of sample being analyzed.

Referring again to FIG. 2, the fluorescence data sets and the Raman data sets are stored database 224 of processing module 220. Database 224 also includes a plurality of known fluorescence data sets and a plurality of known Raman data sets. In one embodiment, the plurality of known fluorescence data sets includes a plurality of fluorescence spectra. In a second embodiment, the plurality of known fluorescence data set includes a plurality of spatially accurate wavelength resolved fluorescence spectroscopic images. In another embodiment, the plurality of known Raman data sets includes one or more of a plurality of Raman spectra. In yet another embodiment, the plurality of spatially accurate wavelength resolved Raman spectroscopic images In database 224, each known fluorescence data set and each Raman data set are associated with a known compound. In one embodiment, the known compound includes suspicious chemical substances such as explosive compounds, a formulation additive of explosive material, a binder of explosive material, a biohazard or an illegal drug. In another embodiment, the known compound includes an explosive compound. Representative known explosive compounds include nitrocellulose, nitroglycerin, 1,3,5-trinitroperhydro-1,3,5-triazine ("RDX"), 1,3,5,7-tetranitroperhydro-1,3,5,7-tetrazocine ("HMX"), and 1,3-Dinitrato-2,2-bis (nitratomethyl)propane ("PETN").

Processor 222 is configured to execute a machine readable program code 226 to search database 224. The database 224 can be searched using a variety of similarity metrics. In one embodiment, the similarity metric produces a score. Representative metrics include Euclidean distance metric, a spectral angle mapper metric, a spectral information divergence metric, a Mahalanobis distance metric and a spectral unmixing algorithm. A spectral unmixing metric is disclosed in U.S. Pat. No. 7,072,770 B1 entitled "Method for Identifying Components of a Mixture via Spectral Analysis," which is incorporated herein by reference in its entirety.

Figures 5A, 5B, 5C, 5D:
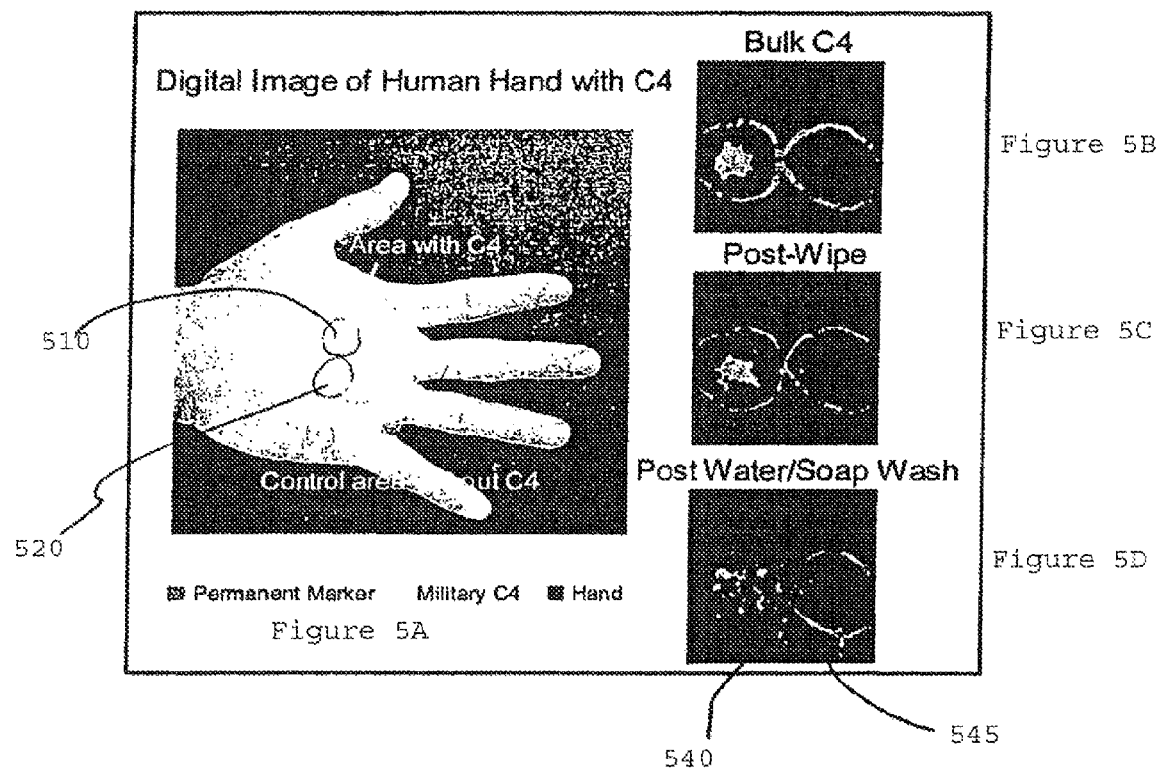
FIGS. 5A-5D illustrate fluorescence images C4 on human skin.

To demonstrate the feasibility of utilizing fluorescence for the detection of residual explosives, military grade C4 explosive was placed on a human hand, FIGS. 5A-5D. FIG. 5A illustrates an image of the hand obtained with ChemImage's CONDOR macroscopic imaging system. A fluorescence chemical image was acquired from an area of interest or location on the skin containing two locations encircled by ink marks—one area of interest 510 containing C4, and one area of interest 520 without C4, FIG. 5A. Fluorescence images were collected immediately after the C4 was placed on the skin FIG. 5B, following a wipe, FIG. 5C, and after the hand was washed with soap and water, FIG. 5D. Using fluorescence imaging, even trace levels of C4 were located in area of interest 540 compared to area 545, after the hand was washed with soap and water. These results are striking and suggest significant sensitivity to trace levels of C4, or more likely, explosives packaging materials.

Figures 6A, 6B:
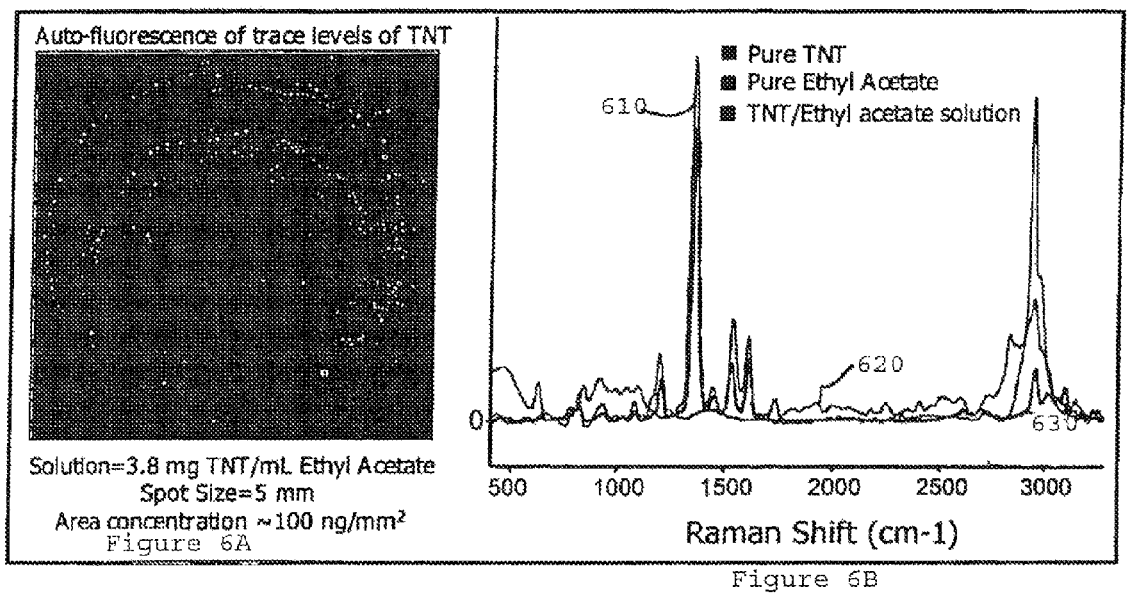
FIG. 6A illustrates fluorescence images of TNT.
FIG. 6B illustrates Raman spectra of TNT.

FIGS. 6A and 6B illustrate fluorescence detection of trace levels of TNT. In FIG. 6A, a fluorescence image shows trace levels of TNT after a sample was treated with 3.8 mg TNT/ml of ethyl acetate. The spot size is 5 mm and the area concentration of TNT was 100 ng/mm$^2$. FIG. 6B illustrates database spectra for pure TNT 610, pure ethyl acetate 620 and TNT in ethyl acetate 630. A Raman signature for TNT was observed at a Raman shift value of approximately 1400 cm$^{-1}$.

Figure 7:
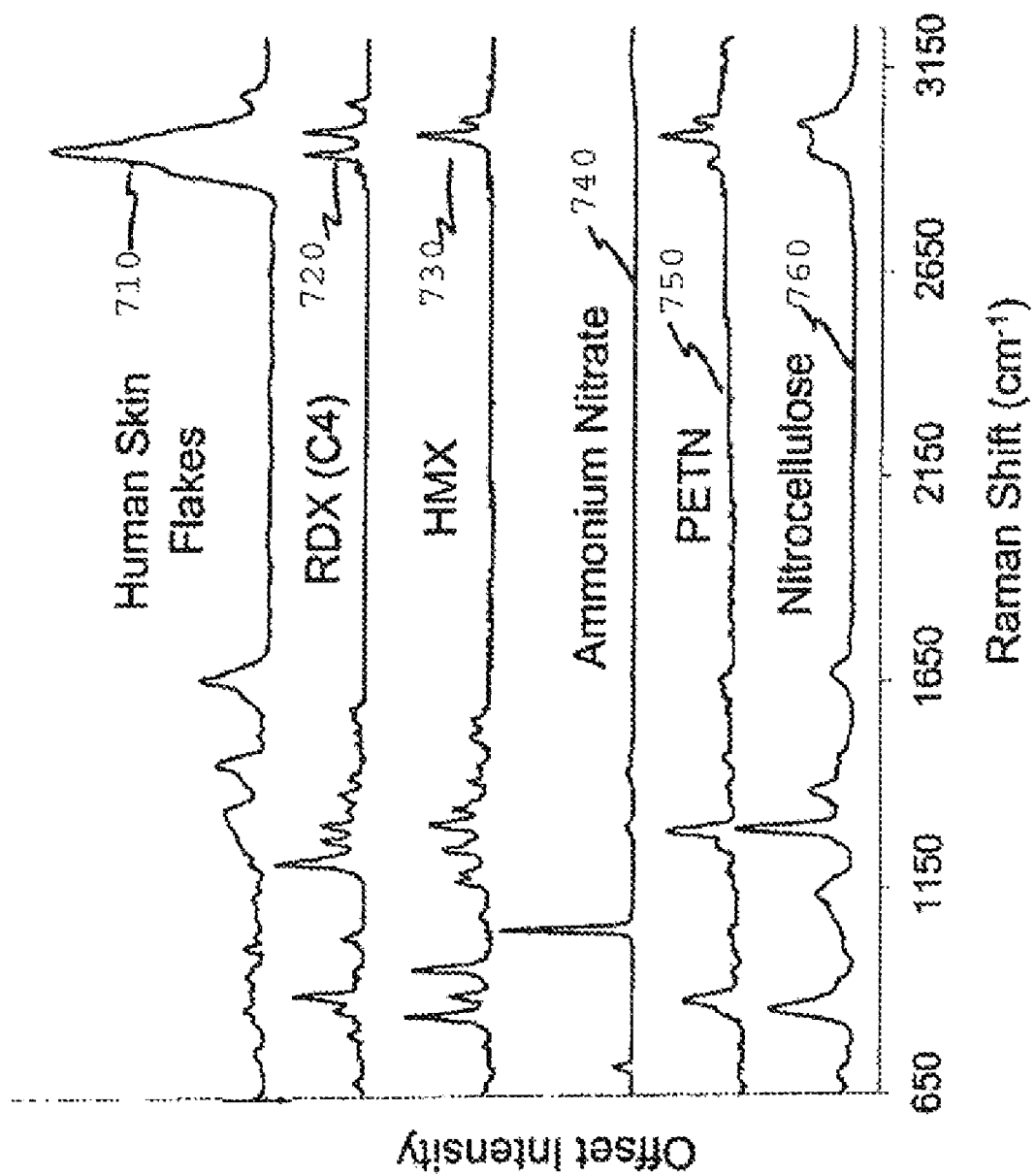
FIG. 7 illustrates Raman dispersive spectra for several explosive materials.

The capability to provide highly specific signatures from representative explosive materials using Raman spectroscopy is illustrated in FIG. 7. The dispersive Raman spectra, include Human skin flakes 710, RDX (C4) 720, HMX 730, Ammonium nitrate 740, PETN 750, and nitrocellulose 760. Each material type exhibits a molecular-specific fingerprint signature. The Raman spectra are inherently rich in information as explosive materials have strong, unique Raman spectra that are "fingerprints" of the vibrational spectrum of the molecule.

Figure 8:
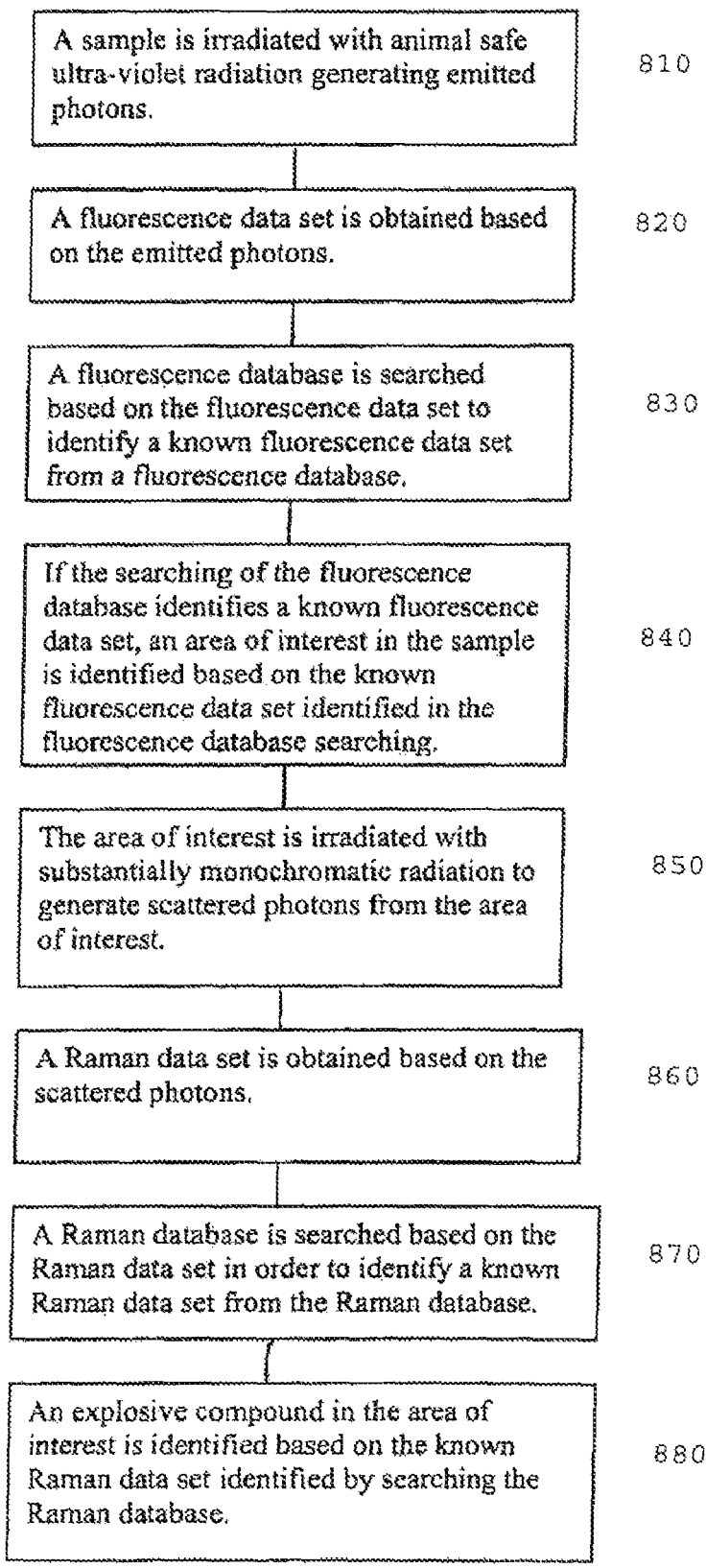
FIG. 8 is a flow chart illustrating an exemplary method of the present disclosure.

Processor 226 is also configured to execute machine readable program code containing executable program instructions to perform a variety of functions. One embodiment is illustrated in FIG. 8 which shows a flow chart for a method of the present disclosure. In step 810, the sample is irradiated with animal-safe ultra-violet radiation to generate emitted photons. In step 820, a fluorescence data set is obtained based on the emitted photons. A fluorescence database is searched, in step 830, in accordance with the fluorescence data set in order to identify a known fluorescence data set from the fluorescence database. The fluorescence database contains a plurality of known fluorescence data sets. Each known fluorescence data set is associated with a known explosive compound. In step 840, if the searching of the fluorescence database identifies a known fluorescence data set, an area of interest in the sample is identified based on the known fluorescence data set identified in the fluorescence database searching. In step 850, the area of interest is irradiated with substantially monochromatic radiation to generate scattered photons from the area of interest. In step 860, a Raman data set is obtained based on the scattered photons. A Raman database is searched, in step 870, based on the Raman data set in order to identify a known Raman data set from the Raman database. The Raman database contains a plurality of known Raman data sets. Each known Raman data set is associated with a known explosive compound. In step 880, an explosive compound in the area of interest is identified based on the known Raman data set identified by searching the Raman database.

Figure 9:
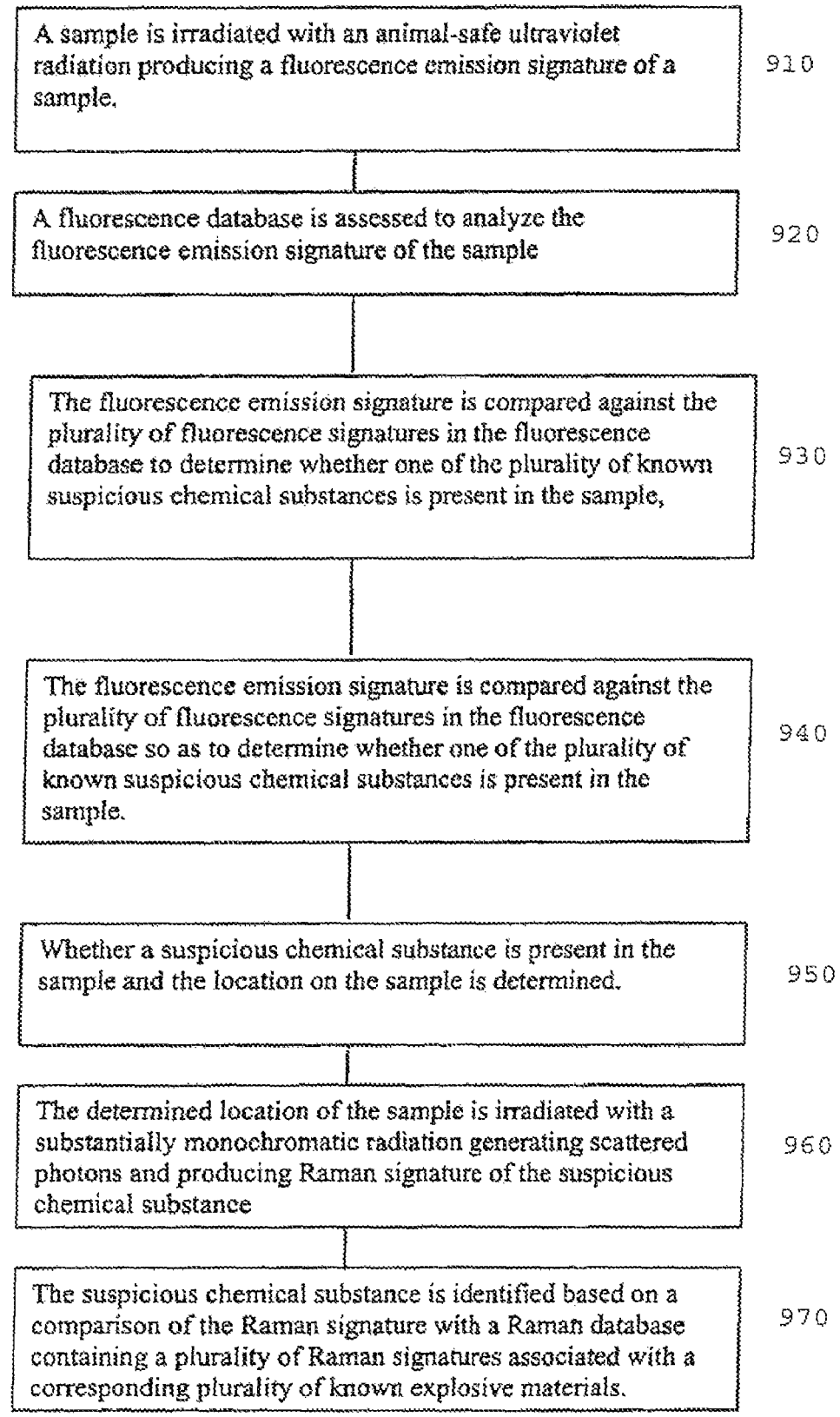
FIG. 9 is a flow chart illustrating an exemplary method of the present disclosure.

Another embodiment is illustrated in FIG. 9 which shows a flow chart for a method of the present disclosure. In step 910, a sample is irradiated with an animal-safe ultraviolet radiation producing a fluorescence emission signature of a sample. To analyze the fluorescence emission signature of the sample, fluorescence database is assessed in step 920. To determine whether one of the plurality of known suspicious chemical substances is present in the sample, the fluorescence emission signature is compared against the plurality of fluorescence signatures in the fluorescence database, in step 930. In step 940, the fluorescence emission signature is compared against the plurality of fluorescence signatures in the fluorescence database so as to determine whether one of the plurality of known suspicious chemical substances is present in the sample. Step 950 determines whether a suspicious chemical substance is present in the sample and the location on the sample. In step 960, the location, determined in step 950, is irradiated with a substantially monochromatic radiation to generate scattered photons producing Raman signature of the suspicious chemical substance. In step 970, the suspicious chemical substance is identified based on a comparison of the Raman signature with a Raman database containing a plurality of Raman signatures associated with a corresponding plurality of known explosive materials.

The present disclosure may be embodied in other specific forms without departing from the spirit or essential attributes of the disclosure. Accordingly, reference should be made to the appended claims, rather than the foregoing specification, as indicating the scope of the disclosure. Although the foregoing description is directed to the preferred embodiments of the disclosure, it is noted that other variations and modification will be apparent to those skilled in the art, and may be made without departing from the spirit or scope of the disclosure.

What is claimed:

1. A method comprising:
   irradiating a sample with animal-safe ultra-violet radiation to thereby generate emitted photons;
   obtaining a fluorescence data set based on the emitted photons;
   first searching a fluorescence database in accordance with the fluorescence data set in order to identify a known fluorescence data set from said fluorescence database, wherein said fluorescence database contains a plurality of known fluorescence data sets, and wherein each known florescence data set is associated with one or more of the following: a known explosive compound, a formulation additive of explosive material and a binder of explosive material;
   if said first searching identifies a known fluorescence data set from said fluorescence database, identifying an area of interest in the sample based on the known fluorescence data set identified in said first searching and irradiating the area of interest with substantially monochromatic radiation to thereby generate scattered photons from said area of interest;
   obtaining a Raman data set based on said scattered photons;
   second searching a Raman database in accordance with the Raman data set in order to identify a known Raman data set from said Raman database, wherein said Raman database contains a plurality of known Raman data sets, and wherein each known Raman data set is associated with a known explosive compound; and
   identifying an explosive compound in the area of interest based on the known Raman data set identified by said second searching.

2. The method of claim 1, wherein said plurality of known fluorescence data sets includes one or more of the following: a plurality of fluorescence spectra corresponding to one or more of the following: a known explosive compound, a formulation additive of explosive material and a binder of explosive material; and a known explosive compound, a formulation additive of explosive material and a binder of explosive material.

3. The method of claim 1, wherein said plurality of known Raman data sets includes one or more of the following: a plurality of Raman spectra corresponding to the known explosive compounds and a plurality of spatially accurate wavelength resolved Raman spectroscopic images corresponding to the known explosive compounds.

4. The method of claim 1, wherein said sample includes one or more of the following: a human hand, a passport, a credit card, a driver's license, a boarding pass, a human body part, a human clothing, a human-wearable item, and an airline ticket.

5. The method of claim 1, wherein said known explosive compound includes one or more of the following: nitrocellulose, nitroglycerin, 1,3,5-trinitroperhydro-1,3,5-triazine ("RDX"), 1,3,5,7-tetranitroperhydro-1,3,5,7-tetrazocine ("HMX"), and 1,3-Dinitrato-2,2-bis (nitratomethyl)propane ("PETN").

6. The method of claim 1, wherein said first searching comprises applying a similarity metric that generates a score.

7. The method of claim 6, wherein said similarity metric comprises one or more of the following: a Euclidean distance metric, a spectral angle mapper metric, a spectral information divergence metric, a Mahalanobis distance metric and a spectral unmixing algorithm.

8. A system comprising:
an animal-safe ultra-violet irradiation source;
a substantially monochromatic irradiation source;
a spectroscopic device;
a fluorescence database having a plurality of known fluorescence data sets, wherein each known fluorescence data set is associated with one or more of the following: a known explosive compound, a formulation additive of explosive material and a binder of explosive material;
a Raman database having a plurality of known Raman sets, wherein each known Raman data set is associated with a known explosive compound;
a machine readable program code containing executable program instructions; and substantially monochromatic irradiation source, and said spectroscopic device and configured to execute said machine readable program code so as to perform the following:
configure said animal-safe ultra-violet irradiation source to irradiate a sample with animal-safe ultra-violet radiation to thereby generate emitted photons;
configure said spectroscopic device to obtain a fluorescence data set based on said photons;
first search said fluorescence database in accordance with the fluorescence data set in order to identify a known fluorescence data set from said fluorescence database;
if said first search identifies a known fluorescence data set from said fluorescence database, identify an area of interest in the sample based on the know fluorescence data set identified in said first searching and configure said substantially monochromatic irradiation source to irradiate the area of interest with substantially monochromatic radiation to thereby generate scattered photons from said area of interest;
configure said spectroscopic device to obtain a Raman data set base don said scattered photons;
second search said Raman database in accordance with the Raman data set in order to identify a known Raman data set from said Raman database; and
identify an explosive compound in the area of interest based on the known Raman data set identified by said second searching.

9. The system of claim 8, wherein said plurality of known fluorescence data sets includes one or more of the following: a plurality of fluorescence spectra corresponding to one or more of the following: a known explosive compound, a formulation additive of explosive material and a binder of explosive material; and a plurality of spatially accurate wavelength resolved fluorescence spectroscopic images corresponding to one or more of the following: a known explosive compound, a formulation additive of explosive material and a binder of explosive material.

10. The system of claim 8, wherein said plurality of known Raman data sets includes one or more of the following: a plurality of Raman spectra corresponding to the known explosive compounds and a plurality of spatially accurate wavelength resolved Raman spectroscopic images corresponding to the known explosive compounds.

11. The system of claim 8, wherein said sample includes one or more of the following: a human hand, a passport, a credit card, a driver's license, a boarding pass, a human body part, a human clothing, a human-wearable item, and an airline ticket.

12. The system of claim 8, wherein said known explosive compound includes one or more of the following: nitrocellulose, nitroglycerin, 1,3,5-trinitroperhydro- 1,3,5-triazine ("RDX"), 1,3,5,7-tetranitroperhydro-1,3,5,7-tetrazocine ("HMX"), and 1,3-Dinitrato-2,2-bis (nitratomethyl) propane ("PETN").

13. A system comprising:
means to irradiate a sample with animal-safe ultra-violet radiation to thereby generate emitted photons;
means to obtain a fluorescence data set based on said emitted photons;
a fluorescence database having a plurality of known fluorescence data sets, and wherein each known fluorescence data set is associated with one or more of the following: a known explosive compound, a formulation additive of explosive material and a binder of explosive material;
means to first search said fluorescence database in accordance with the fluorescence data set in order to identify a known fluorescence data set from said database,
if said first search identifies a known fluorescence data set from said florescence database, means to identify an area of interest in the sample based on the known fluorescence data set identified in said first search and means to irradiate the area of interest with substantially monochromatic radiation to thereby generate scattered photons from said area of interest:
a Raman database having a plurality of known Raman data sets, and wherein each known Raman data set is associated with a known explosive compound
means to second search said Raman database in accordance with the Raman data set in order to identify a known Raman data set from said Raman database; and
means to identify an explosive compound in the area of interest based on the known Raman data set identified by said second search.

14. A storage medium containing machine readable program code, which, when executed by a processor, causes said processor to perform the following:
configure an animal-safe ultra-violet irradiation source to irradiate a sample with animal-safe ultra-violet radiation to thereby generate emitted photons;
configure a spectroscopic device to obtain a fluorescence data set based on said emitted photons;
first search a fluorescence database in accordance with the fluorescence data set in order to identify a known fluorescence data set from said fluorescence database;

if said first search identifies a known fluorescence data set from said fluorescence database, identify an area of interest in the sample based on the known fluorescence data set identified in said first search and configure a substantially monochromatic irradiation source to irradiate the area of interest with substantially monochromatic radiation to thereby generate scattered photons from the area of interest;

configure said spectroscopic device to obtain a Raman data set based on said scattered photons;

second search a Raman database in accordance with the Raman data set in order to identify a known Raman data set from said Raman database; and identify an explosive compound in the area of interest based on the known Raman data set identified by said second search.

15. A method comprising:

obtaining a fluorescence emission signature of a sample, wherein said obtaining said fluorescence emission signature includes irradiating said sample with an animal-safe ultraviolet radiation;

determining whether a suspicious chemical substance is present in said sample and a location of said substance in said sample based on said fluorescence signature of the sample;

irradiating said location on said sample whh.a substantially monochromatic radiation to thereby generate scattered photons therefrom;

obtaining a Raman signature of said suspicious chemical substance based on said scattered photons; and identifying said suspicious chemical substance based on a comparison of said Raman signature with a Raman database containing a plurality of Raman signatures associated with a corresponding plurality of known explosive materials.

* * * * *